United States Patent [19]

Skaptason

[11] Patent Number: 4,971,630
[45] Date of Patent: Nov. 20, 1990

[54] LIQUID HERBICIDAL COMPOSITION HAVING EXTENDED PENETRATING AND SYSTEMIC ACTIVITY

[75] Inventor: Johann S. Skaptason, Leawood, Kans.

[73] Assignee: PBI/Gordon Corporation, Kansas City, Mo.

[21] Appl. No.: 885,388

[22] Filed: Jul. 17, 1986

Related U.S. Application Data

[63] Continuation of Ser. No. 514,239, Jul. 15, 1983, abandoned.

[51] Int. Cl.$^5$ ............................................. H01N 37/38
[52] U.S. Cl. ................................. 71/117; 71/DIG. 1; 71/88; 71/90; 71/94; 71/97; 71/113; 71/115; 71/116
[58] Field of Search ............................ 71/117, DIG. 1

[56] References Cited

U.S. PATENT DOCUMENTS 3,208,843  9/1965  Guth ...................................... 71/117
3,219,429  11/1965 Bucha et al. ...................... 71/DIG. 1
3,907,545  9/1975  Dhingra ............................ 71/DIG. 1
4,266,962  5/1981  Kersting et al. ................. 71/DIG. 1
4,291,497  9/1981  Manankov ....................... 71/DIG. 1
4,396,417  8/1983  Lissant ............................ 71/DIG. 1

FOREIGN PATENT DOCUMENTS 879602  8/1971  Canada ................................. 71/117

Primary Examiner—Glennon H. Hollrah
Assistant Examiner—Raymond Covington
Attorney, Agent, or Firm—Hovey, Williams, Timmons & Collins

[57]  ABSTRACT

A liquid herbicidal composition is disclosed which retains its penetrating and systemic activity after application to susceptible flora under normal ambient conditions for a period of at least six hours by combining at least two different salts of at least one herbicidally active compound and a polyhydric alcohol having 2 to 6 carbon atoms. The salts are preferably amine, ammonium or alkali metal salts of herbicidally active acid halogenated phenoxy acids. The herbicidal composition upon application to noxious vegetation has the unexpected property of retaining its phytotoxic activity throughout the maximum residence time necessary for effective weed and brush control by virtue of the fact that the composition resists crystallization and displays no tendency to either burn or otherwise damage the external cellular layers of the plant being treated.

9 Claims, No Drawings

LIQUID HERBICIDAL COMPOSITION HAVING EXTENDED PENETRATING AND SYSTEMIC ACTIVITY

This application is a continuation of application Ser. No. 514,239, filed Jul. 15, 1983, now abandoned.

BACKGROUND OF THE INVENTION

1. Field of the Invention

This invention relates to herbicidal compositions in liquid form having extended penetrating and systemic activity upon application to susceptible flora. The phytotoxic agent is resistant to initial plant outer cell layer burn that would interfere with its activity but also has been found to be free of such cell damage properties during the extended period of exposure of the plant to the active agent which is a major feature of its total efficacy since the product also resists crystallization for an extended period under normal ambient conditions after application. These desirable characteristics are realized in part because the pH of the material is at least 6 or above at the time of application and remains at such level long periods of time involving many days thus preventing reversion of the toxicant to an acid form which could adversely affect the surface cellular structure of the plants and thus impede the permeation of the material into the plants as well as translocation thereof to the root system.

2. Description of the Prior Art

Acidic herbicides such as 2,4-dichlorophenoxyacetic acid have long been used to control unwanted vegetation. 2,4-D as it is generally known is an insoluble crystalline material having a pH of approximately 2. For convenient application, it is normally converted to liquid form by conversion to water soluble salts or emulsified esters. The ester formulations have been found to be more effective than the salts in the control of noxious vegetation but have the unwanted characteristic of migrating to adjacent desirable vegetation because of the volatility thereof with unacceptable resultant damage.

Efforts to solve the volatility problem including preparation of water soluble salts such as the dimethylamine salt of 2,4-D have not been totally satisfactory because upon volatilization of the amine the herbicide reverts back to its initial acidic form. The acidic composition on the plant surface damages the plant cells thus forming a mechanical barrier of dead tissue which prevents effective penetration of the herbicide into the plant and translocation to all of the above ground and below ground segments.

Canadian Patent No. 879,602 of Ciba-Geigy Canada Ltd. dated Aug. 31, 1971 describes relatively non-volatile herbicidal compositions produced by reacting amines, ammonium, sodium, potassium and lithium compounds with acidic compounds containing for example acid moieties preferably comprising halogenated carboxylic acids, aromatic carboxylic acids, and the halogenated aromatic carboxylic acids, with particularly preferred groups being derivatives of phenoxy acids, and derivatives of benzoic acids. Other groups of compounds are defined as including organo arsenic acids, as well as halogenated aliphatic carboxylic acids. In its preferred embodiments, the compositions of the Canadian Patent involve the mixture of two or more different salts containing the different salts in varying proportions. One or more surfactants are described as being added to the composition causing the liquid to be relatively non-volatile at normal ambient temperature conditions.

Although the formulations of the referenced Canadian '602 Patent did exhibit the desired low volatility, the pH of the herbicidal compositions was sufficiently on the acid side to cause the material to in effect burn the surface layers of the plants on which the herbicide was applied thereby creating a barrier to phytotoxic activity of the herbicide and limiting its effectiveness over desired extended periods of time. As a consequence, the compositions disclosed in the '602 Canadian Patent, although in commercial use, do not lend themselves to use in many aerial applications where extended activity under varying ambient conditions is an essential property of the composition and suffer from the defect of causing plant burn in many instances which significantly reduces its activity in a relatively short period of time after application.

A herbicidal composition especially designed for agricultural spraying is described in Guth U.S. Pat. No. 3,764,293 of Oct. 9, 1973 wherein the patentee suggests that acidic herbicidal agents reacted with metal hydroxides to produce salts are combined with polyhydric diols to assist in dispersion of the herbicidal material in the base water. Here again, the formulation although clearly capable of exhibiting initial herbicidal activity had the tendency to burn the surface cellular structure of susceptible plants which limited activity of the material over extended periods of time and required more frequent application of the phytotoxic agent than is desirable.

SUMMARY OF THE INVENTION

The present invention solves the problems inherent in herbicidal compositions of the prior art by providing an improved formulation prepared from acidic herbicides which can be applied to unwanted vegetation in a physical and chemical form such that the solubilizing agents do not undergo chemical change or volatilize to an extent that the salt can revert back to its acidic form in a relatively short period of time. Instead, a relatively non-acidic herbicidal composition has now been discovered which can be deposited on susceptible flora in a relatively viscous concentrate form which is resistant to reversion back to acidic form. The resulting viscous droplets may reside upon the plant surface without damage to the tissue and are able to penetrate for an extended period of time and translocate to all parts of the plant.

The preferred formulation consists of the dimethylamine and diethanolamine salts of 2,4-D having a pH above 6.0 along with a sufficient quantity of ethylene glycol to cause the liquid herbicidal composition to remain non-crystalline at a pH no less than about 6.0 under normal ambient conditions following application to susceptible flora for a period of at least about six hours. Citric acid as a chelating agent as well as a lignosulfonate type dispersing agent may also be included in the formulation along with an adequate quantity of water to provide a composition of desired viscosity for a particular application.

Preferred formulations having the general characteristics described applied to unwanted vegetation in tolerant crops or in fallow land have been found to exhibit increased herbicidal efficacy over extended periods of time. Deep rooted perennial weeds such as bindweed and leafy spurge normally fully recover and regrow from applications of 2,4-D. However, compositions of the present invention have demonstrably better regrowth inhibition and eventually completely destroy the plants. Data taken from field trials in which Wild Mustard, Lamb's Quarters, Stinkweed, Smartweed, Canada Thistle, Wild Buckwheat, Cowcockle, Volunteer Rape, Tansy Mustard, Hempnettle, Prostrate Pigweed, and Redroot pigweed were present resulted in improved control.

A further advantage exhibited by composition's of this invention is an increase in the amount of deposition of a herbicide in a target area using ultra low volumes from aircraft applications compared to conventional methods of applying similar compounds in usual amounts of water. The normal aircraft application of pesticides occurs under warm dry conditions and the resulting environmental influence produces very small droplets which move from the target area on air currents. The preferred embodiment of the invention results in drops with higher surface tension and a viscosity which combine to result in droplets which resist breakup between discharge from the spray nozzle and the target area. The larger droplets which are airborne for a lesser period of time have a greater propensity to fall within the area of the target than with previous formulations.

DESCRIPTION OF THE PREFERRED EMBODIMENT

The preferred liquid herbicidal composition is made by preparing a liquid mixture of at least two different salts of at least one herbicidally active compound, said salts having a stable pH of no less than about 6.0 being selected from the group consisting of methylamine, ethylamine, isopropylamine, monomethanolamine, monoethanolamine, monoisopropanolamine, dimethylamine, diethylamine, diisopropylamine, dimethanolamine, diethanolamine diisopropanolamine, trimethylamine, triethylamine, triisopropylamine, trimethanolamine, triethanolamine. triisopropanolamine, ammonium, sodium, potassium, and lithium salts of herbicidally active acidic compounds selected from the group consisting of 2,4-dichlorophenoxyacetic acid, 2,4-dichlorophenoxypropionic acid, 2,4-dichlorophenoxybutyric acid, 2-methyl-4-chlorophenoxyacetic acid, 2-methyl-4-chlorophenoxypropionic acid, 2-methyl-4-chlorophenoxybutyric acid, 2,4,5-trichlorophenoxyacetic acid, 2,3,6-trichlorobenzoic acid, 2-methoxy-3,6-dichlorobenzoic acid, 2-methoxy-3,5,6-trichlorobenzoic acid, 4-chloro-2-oxobenzothiazolin-3-ylacetic acid, 4-amino-3,5,6-trichloropicolinic acid, trichloroacetic acid, 2,2-dichloropropionic acid, 3-amino-2,5-dichlorobenzoic acid, methane arsonic acid, 2,3,6-trichlorophenylacetic acid and 3,6-endoxohexahydrophthalic acid. A sufficient quantity of polyhydric alcohol is also included in the composition to cause the product to have characteristics such that it remains a non-crystalline viscous liquid concentrate at a pH of no less than about 6.0 under normal ambient conditions following application to susceptible flora for a period of at least six hours. The preferred eutectic formulation is prepared by use of a polyhydric diol having 2 to 6 carbon atoms or glycerol with best results being obtained when a glycol such as ethylene glycol, 2,3-hexane diol, 2-methyl-2,4-pentane diol, 1,6-hexane diol and 2-methyl-1,2 butane diol or glycerine is employed.

Chelating agents may be added such as citric acid, lactic acid or ethylenediaminetetraacetic acid to stabilize the composition, particularly where water is added as a diluent that may contain various metal or salts of metals.

Dispersing or wetting agents such as a substituted phenyl propane ligno-sulfonates may be added.

A polar solvent such as water may be added to adjust the concentration of the preferred formulation for maximum economic and biological benefit.

The concentrations of salts may vary from 10 to 90 parts by weight of one of the salts and from 10 to 90 parts by weight of a second different salt of the herbicidally active compound with preferred formulations usually being in the range of about 1 part of one salt to about 2 parts of the other salt.

A particularly preferred composition includes on a parts by weight basis of 3.9 parts of 2,4-dichlorophenoxyacetic acid, 1.7 parts of dimethylamine (40%), 0.5 part of diethanolamine (98%), 0.2 part of citric acid, 0.02 part of a substituted phenyl propane ligno-sulfonate, 1 part of ethylene glycol, and 2.6 parts of water. The pH of this composition varies from about 7.6 to about 8.0. Typical tests as recorded herein have demonstrated that this formulation when applied and exposed to ambient conditions will retain a pH exceeding 6.5 for periods up to 20 days.

A specific embodiment of the best mode of this invention is as follows:

| Formula I (Code 736) | |
|---|---|
| Ingredient | Parts by Weight |
| Tech. 2,4-D Acid (98%) | 3.9021 |
| Dimethylamine (40%) | 1.6586 |
| Diethanolamine (98%) | 0.5292 |
| Citric Acid | 0.2100 |
| Marasperse CB* | 0.0178 |
| Ethylene Glycol | 1.0000 |
| Water | 2.5742 |

*Substituted phenyl propane ligno-sulfonate - carbon black dispersion.

A composition of Formula I above was compared with a typical formulation of a Canadian Patent No. 879,602 (hereinafter exemplified by Formula II) and a standard commercial formulation of 2,4-D typically used in agriculture and commerce (hereinafter exemplified by Formula III).

| Formula II (Code EH712-3) | |
|---|---|
| Ingredients | Parts by Weight |
| Tech. 2,4-D Acid (98%) | 4.2133 |
| Dimethylamine (40%) | 1.7736 |
| Diethanolamine (98%) | 1.0075 |
| Igepal CA-630* | 0.4163 |
| Citric Acid | 0.2082 |
| Water | 2.3481 |

*An alkylphenoxypoly (oxyethylene) ethanol

| Formula III (Code 814) | |
|---|---|
| Ingredients | Parts by Weight |
| Dimethylamine Salt of 2,4-D Acid (98%)* | 46.4 |
| Inert Ingredients | 53.6 |

*3.8 parts by weight of 2,4-D acid per gallon (isomer specified in accordance with AOAC Method No. 6 D01-5)

Field tests utilizing Formula I compared with Formula III were conducted on the following species:

| Flora | Abbreviation |
|---|---|
| Lamb's Quarters | LQ |
| Stinkweed | SW |
| Smartweed | SMW |
| Canada Thistle | CT |
| Wild Buckwheat | WB |
| Cowcockle | CC |
| Volunteer Rape | VR |
| Prostrate Pigweed | PPW |
| Redroot Pigweed | RRPW |

WEED CONTROL RATING

LOCATION: 1
Crop: Wheat

| Formula | Rate/A | VR | SMW | CT | WB | LQ |
|---|---|---|---|---|---|---|
| I | 6.6 oz. | 6 | 6 | 6 | 6 | 8 |
| III | 6 oz. | 5 | 5 | 4 | 5 | 7 |
| Untreated | | 0 | 0 | 0 | 0 | 0 |

Crop: Oats, Barley

| Formula | Rate/A | VR | SMW | CT | WB | LQ |
|---|---|---|---|---|---|---|
| I | 6.6 oz. | 9 | 6 | 5 | 5 | 7 |
| III | 6 oz. | 8 | 5 | 5 | 4 | 7 |
| Untreated | | 0 | 0 | 0 | 0 | 0 |

LOCATION: 2
Crop: Barley

| Formula | Rate/A | CT | WB | LQ | RRPW |
|---|---|---|---|---|---|
| I | 8 oz. | 7 | 7 | 7 | 8 |
| III | 8 oz. | 5 | 5 | 7 | 7 |
| Untreated | | 0 | 0 | 0 | 0 |

LOCATION: 3
Crop: Oats, Barley

| Formula | Rate/A | LQ | RRPW | SW | WB | VR | CT |
|---|---|---|---|---|---|---|---|
| I | 8 oz. | 9 | 9 | 9 | 6.5 | 8 | 8 |
| III | 8 oz. | 7 | 7 | 6 | 5 | 7 | 7 |
| Untreated | | 0 | 0 | 0 | 0 | 0 | 0 |

LOCATION: 4
Crop: Wheat

| Formula | Rate/A | LQ | SW | RRPW | PPW | WB | CC |
|---|---|---|---|---|---|---|---|
| I | 8 oz. | 9 | 8 | 8 | 7 | 6 | 5 |
| III | 8 oz. | 8 | 7 | 7 | 6 | 5 | 5 |
| Untreated | | 0 | 0 | 0 | 0 | 0 | 0 |

In all of the four locations in all of the crop species the rating for all treatments for crop tolerance was 9 representing no injury from any of the applications.

In field evaluations in the control of hard to kill, deep rooted perennial weeds applications were made to stands of leafy spurge, Canada Thistle and field bindweed (personnial morning glory). Field data are presented in the following tables:

Leafy Spurge

| | | Average No. of Stems Per Plant | | |
|---|---|---|---|---|
| Formula | Rate | 1980 | 1981 | 1982 |
| I | 4 lb/A | 73.67 | 7 | 1 |
| Untreated | | 63.67 | 70.3 | 83.0 |

Canada Thistle

| | | Average No. of Stems Per Sq. Yd. | | | |
|---|---|---|---|---|---|
| Formula | Rate | 1980 | 1981 | 1982 | 1983 |
| I | 4 lb/A | 176 | 12 | 2 | 1.2 |
| Untreated | | 212 | 213 | 212 | 213 |

Field Bind Weed

| | | Average No. of Stems Per Sq. Yd. | | |
|---|---|---|---|---|
| Formula | Rate | 1980 | 1981 | 1982 |
| I | 3 lb/A | 11 | 3 | 1 |
| Untreated | | 10 | 14 | 9 |

Studies to evaluate the pH of Formulas I, II and III above after the material had been allowed to stand on glass plates under the same ambient conditions for a period of 20 day.

| | pH | |
|---|---|---|
| Formula | Initial | Final |
| I | 7.7 | 6.5 |
| II | 7.5 | 5.0 |
| III | 8.3 | 5.3 |

Leaves from several species of plants were excised and removed to a laboratory where measured droplets of Formulas I, II and III were applied. Observations were made at intervals during a three-day period. Necrotic areas appeared under all of the droplets from Formulas II and III under certain species in a matter of hours and in the others at least by the end of the three-day observation period, but not under the droplets of Formula I. This observation confirms that Formulas II and III sufficiently damaged the epithelial and palisade cells of the plants to an extent that penetration of the herbicide would have been sufficiently inhibited to adversely affect the systemic activity of the composition. These findings relate directly to and explain the efficacy of Formula I as compared with Formula III recorded in the tables above.

I claim:

1. An aqueous liquid herbicidal composition especially adapted for ultralow volume aircraft application while retaining the properties of extended penetrating and systemic activity consisting essentially of:

a mixture consisting essentially of at least two different salts of at least one herbicidally active compound, said salts having a stable pH of no less than about 6, present in amounts providing from 10 to 90 parts by weight of one of said salts and from 10 to 90 parts by weight of a second different salt, and each being selected from the group consisting of methylamine, ethylamine, isopropylamine, monomethanolamine, monoethanolamine, monoisopropanolamine, dimethylamine, diethylamine, diisopropanolamine, dimethanolamine, diethanolamine, diisopropanolamine, trimethylamine, triethylamine, triisopropylamine, trimethanolamine, triethanolamine, triisopropanolamine, ammonium sodium, potassium, and lithium salts of herbicidally active acidic compounds selected from the group consisting of 2,4-dichlorophenoxyacetic acid, 2,4-dichlorophenoxypropionic acid, 2,4-dichlorophenoxybutyric acid, 2-methyl-4-chlorophenoxyacetic acid, 2-methyl-4-chlorophenoxypropionic acid, 2-methyl-4-chlorophenoxybutyric acid, 2,4,5-trichlorophenoxyacetic acid;

a sufficient quantity of water to cause said mixture to be in liquid form; and a sufficient quantity of a polyhydric alcohol selected from the group consisting of polyhydric diols having from 2 to 6 carbon atoms and glycerine which is capable of causing the liquid herbicidal composition to remain noncrystalline as a viscous liquid concentrate and exhibit a pH of no less than about 6 under normal ambient conditions following application to susceptible flora for a period of at least six-hours.

2. A liquid herbicidal composition as set forth in claim 1, wherein said polyhydric alcohol is selected from the group consisting of ethylene glycol, propylene glycol, isopropylene glycol, glycerine, 2,3-hexane diol 2-methyl-2,4-pentane diol, 1,2-pentane diol, 1,6-hexane diol and 2-methyl-1,2 butane diol.

3. A liquid herbicidal composition as set forth in claim 1, wherein said herbicidally active compound is 2,4-dichlorophenoxyacetic acid.

4. A liquid herbicidal composition as set forth in claim 3, wherein one of said salts is the dimethylamine salt of 2,4-dichlorophenoxyacetic acid.

5. A liquid herbicidal composition as set forth in claim 4, wherein one of said salts is the diethanolamine salt of 2,4-dichlorophenoxyacetic acid.

6. A liquid herbicidal composition as set forth in claim 1, wherein said chelating agent is citric acid.

7. A liquid herbicidal composition having extended penetrating and systemic activity comprising the mixture of on a parts by weight basis of 3.9 parts of 2,4-dichlorophenoxyacetic acid, 1.7 parts of dimethylamine (40%), 0.5 part of diethanolamine (98%), 0.2 part of citric acid, 0.2 part of a substituted phenyl propane ligno-sulfonate, 1 part of ethylene glycol, and 2.6 parts of water.

8. A method of controlling noxious vegetation comprising the steps of:

applying to said vegetation by aircraft an effective amount of a liquid herbicidal composition, said composition consisting essentially of a mixture of at least two different salts of at least one herbicidally active compound, said salts having a stable pH of no less than about 6, present in amounts providing from 10 to 90 parts by weight of one of said salts and from 10 to 90 parts by weight of a second different salt, and each being selected from the group consisting of methylamine, ethylamine, isopropylamine, monomethanolamine, monoethanolamine, monoisopropanolamine, dimethylamine, diethylamine, diisopropanolamine, dimethanolamine, diethanolamine, diisopropanolamine, trimethylamine, triethylamine, triispropylamine, trimethanolamine, triethanolamine, triisopropanolamine, ammonium sodium, potassium, and lithium salts of herbicidally active acidic compounds selected from the group consisting of 2,4-dichlorophenoxyacetic acid, 2,4-dichlorophenoxypropionic acid, 2,4-dichlorophenoxybutyric acid, 2-methyl-4-chlorophenoxyacetic acid, 2-methyl-4-chlorophenoxybutyric acid, 2,4,5-trichlorophenoxyacetic acid;

a sufficient quantity of water to cause said mixture to be in liquid form; and a sufficient quantity of a polyhydric alcohol selected from the group consisting of polyhydric diols having from 2 to 6 carbon atoms and glycerine which is capable of causing the liquid herbicidal composition to remain noncrystalline as a viscous liquid concentrate and exhibit a pH of no less than about 6 under normal ambient conditions following application to susceptible flora for a period of at least six hours.

9. A liquid herbicidal composition as set forth in any one of claims 3, 4 or 5 wherein said polyhydric alcohol is ethylene glycol.

* * * * *